United States Patent [19]

Nagai

[11] Patent Number: 4,794,046

[45] Date of Patent: Dec. 27, 1988

[54] IMPLANT MATERIAL WITH CONTINUOUS AND TWO-DIMENSIONAL PORES AND PROCESS FOR PRODUCING THE SAME

[75] Inventor: Hirosi Nagai, Chofu, Japan

[73] Assignee: Kureha Kagaku Kogyo Kabushiki Kaisha, Tokyo, Japan

[21] Appl. No.: 62,660

[22] Filed: Jun. 16, 1987

[30] Foreign Application Priority Data

Jun. 16, 1986 [JP] Japan .................................. 61-139846

[51] Int. Cl.$^4$ ...................... C04B 38/00; C04B 38/06; B32B 3/26
[52] U.S. Cl. ..................................... 428/312.2; 501/1; 501/80; 501/81; 428/312.8; 428/316.6; 428/319.1; 428/701; 428/704
[58] Field of Search ............... 501/1, 80, 81; 428/699, 428/312.2, 312.8, 316.6, 319.1, 701, 704

[56] References Cited

U.S. PATENT DOCUMENTS

| | | | |
|---|---|---|---|
| 4,371,484 | 2/1983 | Inukai et al. | 501/1 |
| 4,376,168 | 3/1983 | Takami et al. | 501/1 |
| 4,503,157 | 3/1985 | Hatchina | 501/1 |
| 4,548,959 | 10/1985 | Hagai et al. | 501/1 |
| 4,654,314 | 3/1987 | Takagi et al. | 501/1 |

FOREIGN PATENT DOCUMENTS 2548661 11/1985 France .
2078696 1/1982 United Kingdom .

*Primary Examiner*—Mark L. Bell
*Attorney, Agent, or Firm*—Nixon & Vanderhye

[57] ABSTRACT

Disclosed herein are a highly strong implant material having continuous passages in the two-dimensional direction, which is a ceramic material of hydroxyapatite and is useful as the substitutive material for bones in the fields of surgery and orthopedics or the filling material in the cavities of bones in the fields of dentistry and oral surgery, and a process for producing the implant material.

8 Claims, No Drawings

IMPLANT MATERIAL WITH CONTINUOUS AND TWO-DIMENSIONAL PORES AND PROCESS FOR PRODUCING THE SAME

BACKGROUND OF THE INVENTION

The present invention relates to a novel ceramic material of hydroxyapatite, which is useful as a substitute material for bones in the fields of surgery and orthopedics or the filling material in a cavities of bones in the fields of dentistry and oral surgery and a process for producing the novel ceramic material. The ceramic material of hydroxyapatite of the present invention is a ceramic material of hydroxyapatite with continuous and two-dimensional pores, which is excellent in its affinity with and an adhesion to the newly formed bones by virtue of having continuous passages in two-dimensional directons, and has the strength necessary to be used as a substitute material for bones by virtue of having a layer of highly compressed ceramic.

Hydroxyapatite has been known as one of the constituent components of bones and teeth and because it is excellent in an affinity with a living body and is not injurious to a living body, hydroxyapatite has been expected as the prosthetic material in a lost part or a cavity of the bone accompanying the fracture of a bone and the erosion of the bone tumor, thus many studies have been carried out concerning the medical use of hydroxyapatite.

Of the studies, porous hydroxyapatite has been proposed as the material which accelerates an activation of the osteophagocytes and the osteoanagenesis cells and is easily able to be fixed into one body with a bone of the host. For instance, in Japanese Patent Application Laid-Open (KOKAI) No. 57-119,745/1982, a three-dimensionally porous prosthetic material of the mean diameter of the internally continuous openings of 0.1 to 8 mm and of the porosity of not less than 60% has been disclosed and in Japanese Patent Application Laid-Open (KOKAI) No. 60-16,879/1985, a porous material in which the internal openings of a diameter of 1 to 600 $\mu$m have been connected to outside space by capillary vessels of a diameter of 1 to 30 $\mu$m has been proposed.

However, when a material is made porous, the reduction of its strength is generally unavoidable and such a material is not necessarily satisfactory in the point of porous hydroxyapatite which is excellent in an affinity with a living body and has a practically reliable mechanical strength.

As a result of the present inventor's earnest studies, while considering the above situations, for developing an implant material which is excellent in an affinity with and an adhesion to the newly formed bone and is high in strength, it has been found by the present inventors that the porous hydroxyapatite which is obtained by a specific process and has the two-dimensional and continuous pores (passages) is in conformity with the object of the present invention and on the basis of their findings, the present invention has been attained.

SUMMARY OF THE INVENTION

The object of the present invention lies in providing a novel ceramic material of hydroxyapatite, which is useful as a substitute material for bones in the fields of surgery and orthopedics or as a filling material in the cavities of bones in the field of dentistry and oral surgery.

Furthermore, an object of the present invention lies in providing a ceramic material of hydroxyapatite, which material is characterized in that the material has the continuous passages in two-dimensional directions.

Still more, an object of the present invention lies in providing a ceramic material of hydroxyapatite, which is excellent in an affinity with and an adhesion to the newly formed bone and retains a necessary strength as the substitute material for bones.

Moreover, an object of the present invention lies in providing a process for producing the ceramic material of hydroxyapatite, which is in conformity with the above objects.

DETAILED DESCRIPTION OF THE INVENTION

The present invention relates to a novel ceramic material of hydroxyapatite, which is produced by press-molding a laminated body comprising a layer of net made of natural or synthetic fibers and a layer of natural or synthetic powdery hydroxyapatite, by heat-decomposing the net made of fibers and then by sintering the press-molded, laminated body under an ordinary pressure or an applied pressure. The resulting product is characterized in having the continuous passages therein, is excellent in its affinity with and an adhesion to newly formed bones and has sufficient strength as a substitute material for bones in the fields of surgery and orthopedics or a filling material in the cavities of bones in the field of dentistry and oral surgery.

The ceramic material with continuous and two-dimensional pores according to the present invention (hereinafter referred to as the ceramic material of the present invention) can be produced by the following process:

The ceramic material of the present invention is produced after alternately piling up the unfired or provisionally fired powdery hydroxyapatite and the nets made of natural or synthetic fibers, preparing a piled and molded body from the piled body while using a press-molding method, etc., heat-decomposing and gasifying the net at the temperature of 200° to 500° C. and then firing the piled and molded body at a temperature of 900° to 1400° C.

As the hydroxyapatite, synthetic or natural hydroxyapatite or the fired product thereof and a mixture thereof may be exemplified.

The synthetic hydroxyapatite can be produced by any publicly known method and for instance, it is synthesized by a dry synthetic method wherein $Ca_3(PO_4)_2$ and an excess of $CaCO_3$ are brought into reaction in a flow of steam of a high temperature of 900° to 1300° C. as described in "Ceramics", Vol. 10 (7), page 461 (1975), a method wherein an emulsion of fine-particle calcium hydroxide and an aqueous solution of phosphoric acid are brought into reaction under a high speed agitation (refer to Japanese Patent Application Laid-Open (KOKAI) No. 56-45,814/1981) or a wet synthetic method wherein an aqueous solution of $Ca(NO_3)_2$ and an aqueous solution of $NH_4H_2PO_4$ are brought into reaction under a $NH_4OH$-alkaline state (refer to "Angewandte Chemie", 67, 327 (1955)).

The natural hydroxyapatite can be obtained from natural bones as the raw material. For instance, cow's bones are calcined at a temperature around 800° C. to remove organic materials therefrom and the natural hydroxyapatite is obtained. When necessary, the hydroxyapatite can be the material containing β-witlockite or a different element such as fluorine, iron, etc.

The diameter of powdery hydroxyapatite particle should not be larger than 1000 μm taking into consideration of the processability in molding and the handling thereof, and. is preferably 0.01 to 200 μm, and more preferably 0.1 to 100 μm.

The powdery hydroxyapatite of the above particle size is available, for instance, by a method wherein coarse particles of hydroxyapatite are pulverized in the presence of an organic solvent with a ball mill. The pulverizing method is profitable compared to the ordinary method in the point that the time for pulverizing can be shortened and in case of necessity, the step of classification or the step of freeze-drying, which is necessary when water is used, can be omitted. As the organic solvent, it is preferable to use a solvent of a relatively low boiling point such as acetone, hexane and alcohols.

The fabricated or molded net used in the present invention is used to form the two-dimensional and continuous passages by heat-decomposition and gasification (disappearance) of the net material by sintering the piled and molded body comprising hydroxyapatite and the net and accordingly, it is preferable that the net is made of non heat-shrinkable organic polymer so that the piled and molded body is not deformed in the step of sintering. As the organic polymer, thermosetting synthetic polymer such as polyimide, triethyene glycol dimethacrylate and polyester, thermoplastic synthetic polymer such as polymethyl methacrylate, polystyrene, polyvinyl acetate and polypropylene polyethylene or natural polymer such as cellulose and collagen may be exemplified.

Although the diameter of the organic polymer can be properly selected according to the desired diameter of the passages in the ceramic material, it is preferable to use monofilaments of a diameter in the range of 20 to 2000 μm from the view point of the affinity of pores to a living body (invasion of the fibrous tissue and ability to forming bones).

The size of the aperture of the fabricated or molded net comprising the organic polymer can be properly selected according to the desired porosity of the ceramic material and the size is generally in the range of 0.5 to 5 mm, preferably 1 to 2 mm.

When piling the fabricated or molded net and hydroxyapatite, hydroxyapatite is used in the powdery state or after being slurried with water or an organic solvent.

After piling up the fabricated or molded net and hydroxyapatite, the piled body is subjected to press-molding to obtain the piled and molded body of the desired shape. For molding the piled body by a press-molding method, the press method at ordinary temperature, the hot-press method or the rubber press method is used singly or by combination thereof.

The ceramic material of the present invention can be produced by firing the piled and molded body at a temperature of 900° to 1400° C. Although the firing may be carried out without applying a pressure, the firing can be carried out also applying a pressure of 300 to 1000 kg/cm$^2$, for instance, using a hot-press.

When the ceramic material of the present invention, which is prepared by the process mentioned above, is applied to the use for the artificial bone or the artificial jawbone, judging from the stand point of mechanical strength and biocompatibility, the ceramic material having the porosity of 20 to 90% and the continuous openings of a mean diameter of 50 to 1500 μm in the two-dimensional directions is suitable.

In the case of applying the ceramic material of the present invention, for instance, to the jawbone, the ceramic material is to be placed so that the porous part of the material contacts the natural bone and the compact part of the material contacts the gum.

Besides, the ceramic material of the present invention, which is calcined as a piled and molded body of a shape of concentric centers instead of a flat-type, has continuous and two-dimensional pores along the perifery of each circles and the utility of such a type of the ceramic material for the artificial bone is large.

The ceramic material of the present invention can crushed and used as a filling material in the cavities of the bones in a form of powder not only for use as the surgical implant material.

The present invention will be described more in detail while referring to the non-limitative Examples as follows:

EXAMPLE 1

The filtered and dried cake of synthetic hydroxyapatite obtained by bringing an emulsion of fine-particle calcium hydroxide and an aqueous solution of phosphoric acid into reaction under a high speed agitation was pulverized into particles of a diameter of about 5 mm in a mortar, and the obtained particles were supplied into a ball mill. After adding acetone in an amount of 3 times by volume of the particles into the ball mill, the particles were further pulverized to obtain a fine-particle material of a mean diameter of 25 μm.

Separately, six pieces of a molded net of synthetic fiber of polymethyl methacrylate (diameter of the filament of 1 mm) of an aperture of 2 mm were cut from the whole net in the size of the metal mold (100 mm in length and 50 mm in width) for use as the female mold of the openings of the ceramic material. In this case, the ceramic material with continuous pores was set up to be 40% in porosity and 10 mm in thickness.

In a metal mold, one of the six pieces of net was placed and 15.7 g of the fine-particle hydroxyapatite were placed on the net evenly.

The remaining pieces of the net were piled up with the hydroxyapatite in the same manner as described above. Thereafter, the piled body in the metal mold was press-molded under a pressure of 200 kg/cm$^2$ and then, the press-mold body was further press-molded under a pressure of 1,000 kg/cm$^2$ with a rubber press. The further press-molded body was heated at 400° C. for five hours to decompose and gasify the net of polymethyl methacrylate and then fired for one hour at 1200° C.

Thus, a sintered body of hydroxyapatite having uniform, continuous and two-dimensional passages (pores) of a mean porosity of 40% was obtained. The flexural strength of the sintered body was 150 kg/cm$^2$.

EXAMPLE 2

After provisionally firing the coarse particles of hydroxyapatite of the filtered and dried cake described in Example 1 for 3 hours at 800° C., the obtained coarse particles were pulverized into fine particle of a diameter of not more than 25 μm in the same manner as in Example 1.

Separately, 12 pieces of a molded net of polystyrene (diameter of the filament 500 μm) of an aperture of 2 mm were cut from the whole net in the size of 100 mm in length and 50 mm in width for use as the female mold of the openings of the ceramic material. In this case, the ceramic material with continuous pores was set up to be 40% in porosity and 10 mm in thickness as in Example 1.

The amount of the fine-particle hydroxyapatite placed in the metal mold was set up to 7.8 g/net, and hydroxyapatite and the nets were piled up in the same manner as in Example 1.

Thereafter, the piled materials in the metal mold were press-molded under a pressure of 200 kg/cm$^2$ and further press-molded by a rubber press of a pressure of 1000 kg/cm$^2$, and then, the further molded body was heated for five hours at 400° C. to decompose and gasify the polyethylene net and then fired for one hour at a temperature of 1350° C.

Thus, a sintered body of hydroxyapatite having the uniform, continuous and two-dimensional passages of a mean diameter of 500 μm and a porosity of 40% was obtained. The flexural strength of the sintered body was 210 kg/cm$^2$ in the average.

EXAMPLE 3

After cut-processing the sintered bodies of hydroxyapatite obtained in Examples 1 and 2 into a semicylindrical shape of a size of 10 mm in length, 20 mm in width and 10 mm in height and sterilizing the cut bodies with high pressure steam according to an ordinary method, the sterilized bodies were implanted into the mandibular base of a shepherd dog of a body weight of 35 kg.

After 6 months of the implantation, the shepherd dog was sacrificed and the pathological specimen of the hard tissues of the implanted region was prepared and examined. As the results, according to the findings of an X-ray photograph of the hard tissue, it was found that the formation of bones reached to the central part of implanted body. On the other hand, according to the finding of the de-calcium specimen, the invasion of the fibrous tissue and the blood vessels into the newly formed bone was confirmed.

According to the above-mentioned findings, it was recognized that the ceramic material of the present invention having continuous and two-dimensional pores can be used clinically as a reinforcing material to defective parts in the manibula.

What is claimed is:

1. A ceramic material of hydroxyapatite having continuous and two-dimensional pores therein, wherein said ceramic material has continuous passages in the two-dimensional directions.

2. A ceramic material of hydroxyapatite having continuous and two dimensional pores according to claim 1, wherein said continuous passages have the mean diameter of from 50 to 1500 μm and the porosity of said ceramic material is from 20 to 90%.

3. A process for producing a ceramic material of hydroxyapatite having continuous and two-dimensional pores therein, comprising the steps of: (1) laying up alternating layers of hydroxyapatite and a heat decomposible net or organic polymer in a laminated state, one upon the other, in a mold (2) heat-decomposing and gasifying the net material, and then (3) firing the thus plied and molded body in which hydroxyapatite and fabricated or molded net or organic polymer have been piled up in a laminated state to form the continuous, two-dimensional network of pores in the ceramic material.

4. A process for producing a ceramic material of hydroxyapatite having continuous and two-dimensional pores according to claim 3, wherein said fabricated or molded net of organic polymer is a non heat-shrinkable.

5. A process for producing a ceramic material of hydroxyapatite having continuous and two-dimensional pores according to claim 3, wherein said fabricated or molded net of organic polymer comprises polyimide, triethylene glycol dimethacrylate, polyester, polymethyl methacrylate, polystyrene, polyvinyl acetate, polypropylene, cellulose or collagen.

6. A laminated press molded, sintered layered ceramic structure composed of a plurality of alternating substantially parallel layers, one stacked upon the other, of solid hydroxyapatite and porous hydroxyapatite in which the pores are continuous passages in two directions substantially perpendicular with each other and parallel to the porous layer, respectively.

7. The laminated, layered ceramic structure of claim 6, in which the porous layers have a porosity of from 20 to 90%.

8. The laminated, layered ceramic structure of claim 6, in which the mean diameter of the pores in the porous layers is from 50 to 1500 μm.

* * * * *

UNITED STATES PATENT AND TRADEMARK OFFICE
CERTIFICATE OF CORRECTION

PATENT NO. : 4,794,046
DATED : December 27, 1988
INVENTOR(S) : Hirosi NAGAI It is certified that error appears in the above-identified patent and that said Letters Patent is hereby corrected as shown below:

Column 1, line 11, "a" should read --the-- after "in".

Column 2, line 26, delete "the ".

Column 4, line 15, after "can" add --be--.

Column 4, line 56, after "mean" insert --diameter of 1,000 um and a--.

Column 5, line 17, delete "the".

Column 5, line 45, correct the spelling of "mandibula".

IN THE CLAIMS:

Column 6, Claim 2, line 7, delete "the" and insert --a--.
Column 6, Claim 3, line 14, "or" should read --of--;
line 15, a comma following "mold" is needed to properly display the claim; and
line 18, "or" (second occurrence) should read --of--.

Signed and Sealed this

Twenty-seventh Day of March, 1990

*Attest:*

JEFFREY M. SAMUELS

*Attesting Officer*     *Acting Commissioner of Patents and Trademarks*